United States Patent
Beulay et al.

(10) Patent No.: US 8,163,172 B2
(45) Date of Patent: *Apr. 24, 2012

(54) INSTALLATION FOR TREATING A BIOLOGICAL LIQUID

(75) Inventors: Jean-Luc Beulay, Krautergersheim (FR); Virginie Buisson, Wolfisheim (FR); Sebastien Cirou, Schiltigheim (FR); Cecile Delbos, Eschau (FR); Marc Hlavacek, Phalsbourg (FR); Frans Mels, Altenmarkt (AT); Rene Reinbigler, Kirchheim (FR); Jean-Louis Weissenbach, Barr (FR)

(73) Assignee: EMD Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/079,188

(22) Filed: Apr. 4, 2011

(65) Prior Publication Data

US 2011/0174716 A1   Jul. 21, 2011

Related U.S. Application Data

(63) Continuation of application No. 12/455,175, filed on May 29, 2009, now Pat. No. 7,935,253.

(30) Foreign Application Priority Data

Jun. 2, 2008   (FR) .................................. 08 53629

(51) Int. Cl.
  *B01D 36/00* (2006.01)
  *C12M 1/12* (2006.01)
(52) U.S. Cl. ....... 210/90; 210/241; 210/416.1; 422/534; 422/565; 422/566; 435/297.1

(58) Field of Classification Search ............... 210/241, 210/257.1, 257.2, 416.1, 90; 435/297.1; 422/534, 535, 565, 566
See application file for complete search history.

(56) References Cited

U.S. PATENT DOCUMENTS 3,022,229 A   2/1962   Heden
(Continued)

FOREIGN PATENT DOCUMENTS

EP   0479047 A2   4/1992
(Continued)

OTHER PUBLICATIONS

French Search Report dated Feb. 9, 2009 in corresponding foreign patent application No. FR 0853629/FA 708766.

(Continued)

*Primary Examiner* — Christopher Upton
(74) *Attorney, Agent, or Firm* — Nields, Lemack & Frame, LLC

(57) ABSTRACT

Installation for treating a biological liquid, including a circulation pump (5), a filter element (9), a container for collecting treated liquid, a first circuit section connecting a source of said biological liquid to an inlet orifice of said filter element (9), including a circuit element adapted to cooperate with said circulation pump (5); a second circuit section, connecting an outlet orifice of said filter element (9) to said treated liquid collecting container; characterized in that said treated liquid collecting container, said first circuit section and said second circuit section are disposable and said installation further includes a first cart (1) carrying said pump (5) and a second cart (2) including a housing (14) for said collecting container, separable from the first cart (1) and adapted to be at least partly nested in said first cart (1).

14 Claims, 6 Drawing Sheets

U.S. PATENT DOCUMENTS

| | | | |
|---|---|---|---|
| 4,113,623 | A | 9/1978 | Koether et al. |
| 5,141,866 | A | 8/1992 | Levin |
| 5,520,885 | A | 5/1996 | Coelho et al. |
| 6,228,255 | B1 | 5/2001 | Peterson et al. |
| 7,935,253 | B2 | 5/2011 | Beulay et al. |
| 2004/0104153 | A1 | 6/2004 | Yang |
| 2004/0259240 | A1 | 12/2004 | Fadden |
| 2005/0254879 | A1 | 11/2005 | Gundersen et al. |
| 2006/0024212 | A1 | 2/2006 | Hwang |
| 2007/0199875 | A1 | 8/2007 | Moorey et al. |
| 2010/0206785 | A1 * | 8/2010 | Beulay et al. ............ 210/85 |

FOREIGN PATENT DOCUMENTS

| | | | |
|---|---|---|---|
| EP | 0803723 | A1 | 10/1997 |
| EP | 1239277 | A1 | 9/2002 |
| EP | 2044964 | A2 | 4/2009 |
| FR | 2241615 | A1 | 3/1975 |
| FR | 2673853 | A1 | 9/1992 |
| FR | 2931838 | A1 | 12/2009 |
| FR | 2940145 | A1 | 6/2010 |
| WO | 00/48703 | A1 | 8/2000 |
| WO | 2005/090403 | A2 | 9/2005 |
| WO | 2006/043895 | A1 | 4/2006 |

OTHER PUBLICATIONS

Extended European Search Report for co-pending foreign patent application No. EP 09290938.1, mailed Apr. 6, 2010, 5 pages.

French Search Report dated May 24, 2011 in co-pending foreign patent application No. FR 1056421.

* cited by examiner

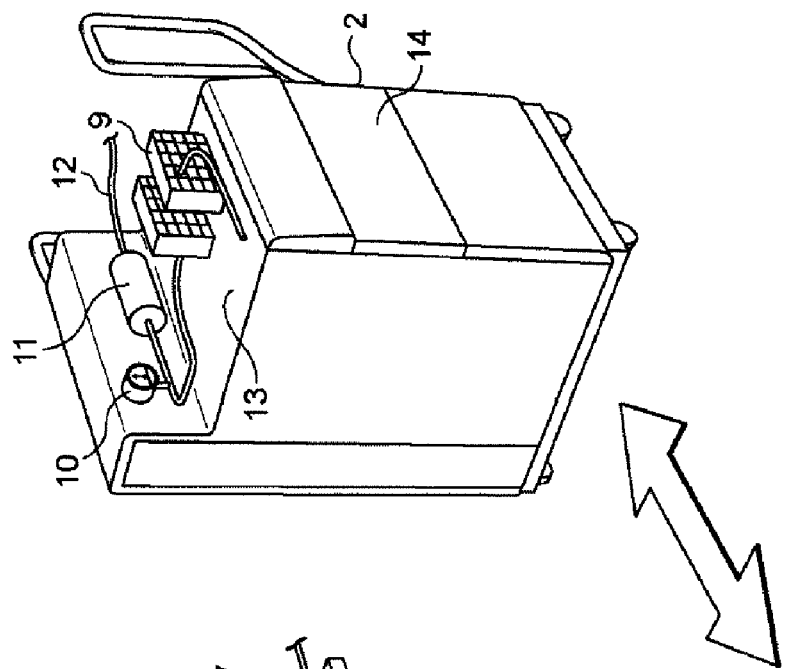
Fig. 2
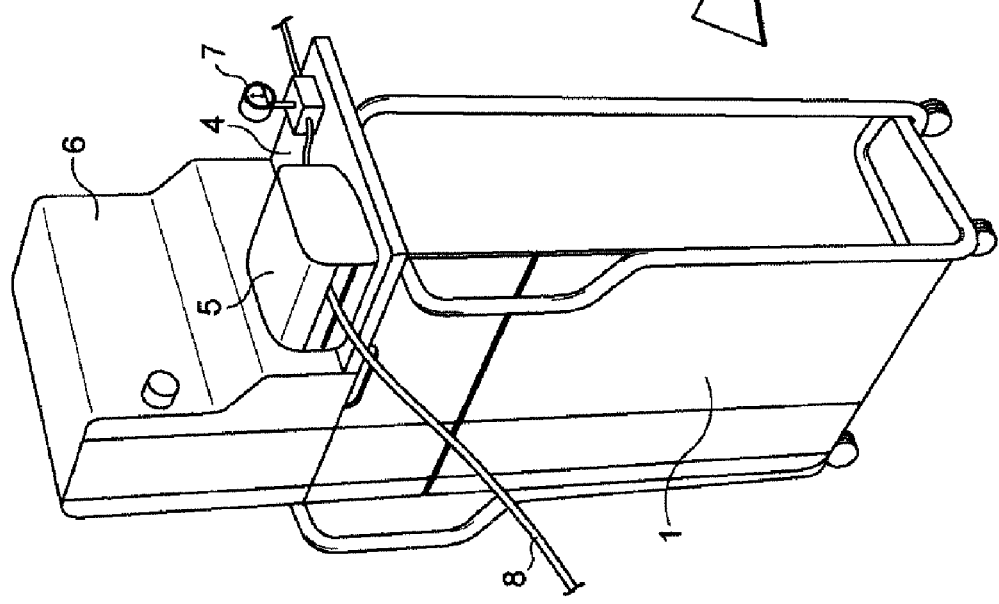
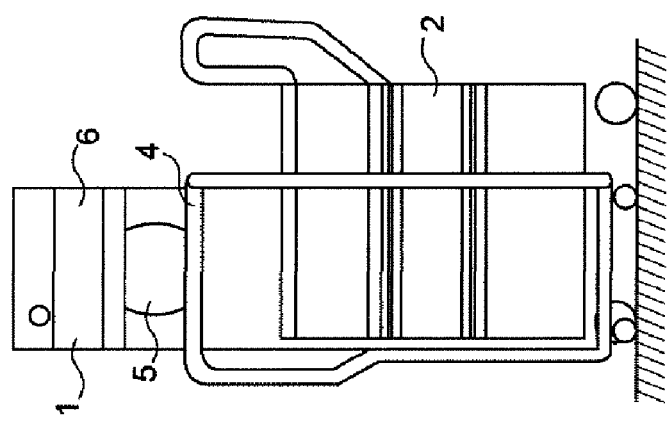
Fig. 1

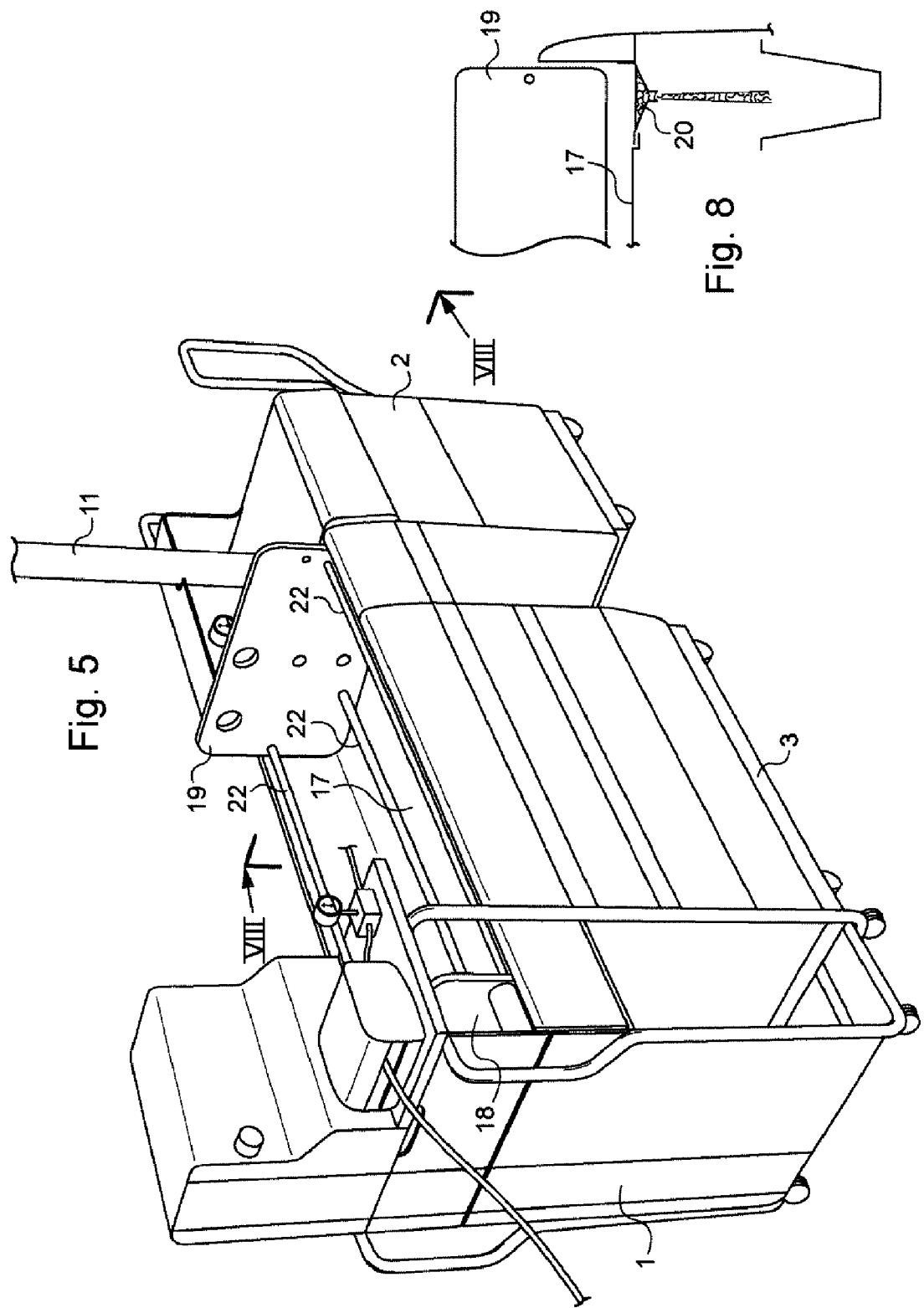

INSTALLATION FOR TREATING A BIOLOGICAL LIQUID

This application is a continuation of U.S. Ser. No. 12/455,175 filed May 29, 2009, the disclosure of which is incorporated herein by reference.

The invention relates to installations for treating a biological liquid, in particular, but not exclusively, for purifying a biopharmaceutical liquid in order to obtain products such as monoclonal antibodies, vaccines or recombinant proteins.

Biopharmaceutical liquids are generally obtained by culture in a bioreactor and must then be purified to achieve the required characteristics in terms of concentration, absence of viruses, etc.

Purification generally includes a clarification treatment to eliminate residues of the bioreactor culture and virus retention treatment, sometimes followed by diafiltration and tangential flow filtration (TFF) treatment. Other purification treatments include chromatography and sterile filtration (to remove bacteria).

Purification treatment is effected essentially by filtering operations in a circuit leading to a container for collecting the treated liquid.

A number of types of container containing liquids can be connected to the inlet of the circuit, such as the source container that contains the product to be treated, and also containers containing a cleaning or rinsing liquid, a buffer liquid or a neutral liquid such as pure water.

In addition to the container for collecting the treated liquid, various other cleaning, rinsing or buffer liquid collecting containers or by-product or residue collecting containers can be connected to the outlet of the circuit.

In a production context the liquid treatments can be carried out sequentially, the collection container for the first treatment potentially becoming the source container for the next treatment, and so on until the last treatment is carried out.

These treatments are conventionally carried out in dedicated circuits, with stainless steel pipes and other components such as tanks and filter housings, which necessitate operations before and after treatment as such that are relatively heavy, in particular operations of cleaning after use.

The invention aims to provide an installation for treating a biological liquid that is particularly simple, convenient and effective.

To this end the invention proposes an installation for treating a biological liquid, including:
  a circulation pump;
  a filter element;
  a container for collecting treated liquid;
  a first circuit section connecting a source of said biological liquid to an inlet orifice of said filter element, including a circuit element adapted to cooperate with said circulation pump to circulate said biological liquid in said first circuit section; and
  a second circuit section, connecting an outlet orifice of said filter element to said treated liquid collecting container;
  characterized in that said treated liquid collecting container is a disposable bag, said first circuit section and said second circuit section are disposable and said installation further includes:
    a first cart carrying said pump; and
    a second cart including a housing for said collecting bag, separable from the first cart and adapted to be at least partly nested in said first cart.

The installation of the invention therefore includes disposable elements, for the most part flexible ("Flexware™ products"), including the treated liquid collecting bag and the circuit sections, even the filter element, and permanent or reusable elements ("hardware") accommodated in two or more carts.

An installation of the invention is simply assembled by equipping the carts with the disposable elements, in particular with the circuit element adapted to cooperate with the circulation pump, which is installed on the pump, and with the treated liquid collecting bag, which is housed in a carriage other than that carrying the pump.

The fact that the two carts can be separated facilitates the fitting of the collecting bag and even the fitting of the various circuit sections.

The fact that the cart housing the treated liquid collecting bag can then be at least partially nested in the cart that carries the pump optimizes the footprint required for the installation of the invention.

This possibility of optimizing the footprint is particularly advantageous when, as is generally the case in treatment of biopharmaceutical liquids, the installation is placed in a controlled atmosphere area where space is at a premium.

Finally, the post-treatment steps are essentially the removal and discarding of the disposable elements. This is just as simple to carry out as the preparation of the installation, in particular because the carts can be separated.

According to features that are preferred as being favorable to the simplicity and convenience of use of the installation of the invention:
  when said second cart is nested at least partly in said first cart, said housing for said collecting bag is positioned at least partly under said pump;
  said first cart includes a control panel of said pump;
  said housing of said second cart is formed by the interior of a drawer;
  the front of said drawer includes a notch adapted to have a pipe of said second circuit section pass through it;
  the first cart has a length less than that of the second cart;
  said first cart has a globally parallelepiped shape open on one side and at the bottom to enable nesting of said second cart;
  said first circuit section includes a pre-filter element between the outlet orifice of said circulation pump and the inlet orifice of said filter element;
  said installation includes a third cart including a support for said filter element and an alternate housing for said collecting bag, said third cart being adapted to be disposed between the first cart and the second cart;
  said third cart is adapted to be nested at least partly in said first cart and to be disposed side by side with the second cart;
  said alternate housing is a tank on wheels adapted to contain said bag;
  at least one of said carts includes a plurality of housings for a disposable bag;
  at least one of said carts includes a plate sliding like a drawer and provided with a liquid evacuation plughole;
  each of said carts is mounted on wheels; and/or
  said second circuit section includes a final filter element between the outlet orifice of said filter element and said collecting bag.

The disclosure of the invention continues next with a description of preferred embodiments, given hereinafter by way of nonlimiting illustration and with reference to the appended drawings. In the drawings:

FIG. 1 is a highly diagrammatic view in elevation of an installation of the invention in a nested configuration;

FIG. 2 is a more detailed perspective view of this installation in a separated configuration;

FIG. 5 is a view similar to FIG. 4 for another variant with three carts;

FIG. 8 is a partial view in elevation and in section taken along the plan VIII-VIII in FIG. 5;

FIG. 1 shows an installation for treating a biological liquid including a first cart 1 and a second cart 2 in a nested configuration, i.e. with the second cart 2 partially nested in the first cart 1. The length of the first cart 1 is shorter than that of the second cart.

FIG. 2 shows the same installation with two carts in a separated configuration, i.e. with the second cart 2 moved away from the first cart 1.

Figure 3:
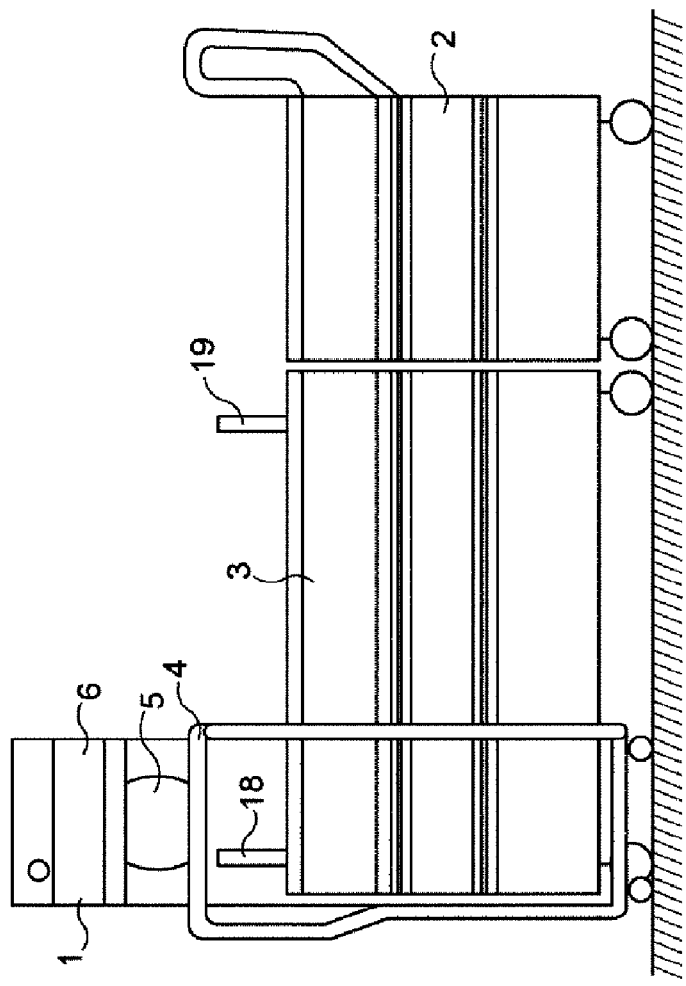
FIG. 3 is a view similar to FIG. 1 of a variant including a third cart, in the nested configuration.

FIG. 3 shows an installation including a third cart 3, in a nested configuration, i.e. with the third cart 3 partially nested, on its left-hand side, in the first cart 1. FIG. 5 shows a variant in which the third cart 3 is longer.

In another variant non-illustrated, the carts are designed such that the right-hand side (and not the left-hand side) of the second or the third cart is nested within the first cart.

The biological liquid treatment circuit produced with the aid of disposable elements installed on the carts described above is described first, with reference to FIG. 9, in the case of a clarification treatment.

The product to be treated is initially in a source bag 31, coming from the culture bioreactor or from the previous treatment. This source bag 31 is connected via a male connector 35 to a first circuit section 60 which goes from the source bag to an inlet point 37 of a filter element 9. The male connector 35 is connected to a first disposable flexible pipe 8, which is itself fitted with a female connector 36. In a variant that is not shown the gender of connectors 35 and 36 are inverted or they are genderless connectors. The operator can connect to the first flexible pipe other bags 32 or 34 containing products such as a buffer liquid or a rinsing liquid such as pure water, respectively, for controlling the cleanliness of the circuit or for pushing the liquid to be treated toward the elements that carry out the treatment. These alternative bags are also fitted with a connector 35 adapted to cooperate with connector 36 on the first flexible pipe 8. In a variant that is not shown, the flexible pipe 8 carries both a female connector like the connector 36 and a genderless connector. Isolating valves or clamps are also fitted to the flexible pipes upstream and downstream of these connectors to enable or prevent circulation of the liquid in the flexible pipe.

When the flexible pipe is open and the pump 5 is running, the biological liquid is sucked from the source bag into the first flexible pipe 8. This first flexible pipe 8 carries a circuit element 8a adapted to cooperate with the circulation pump 5, whether the latter is a peristaltic pump or some other pumping system. The first flexible pipe, identified by the reference number 8b in the figures, downstream of the circulation pump 5 is connected to a first pressure sensor 7 that measures the pressure on the upstream side of a filter element 9. Its other end is connected to the inlet orifice 37 of the filter element 9.

The circulation pump 5 causes the liquid to be treated to pass through the filter element 9 in which it is clarified, leaving most of the bioreactor culture residue behind, then entering a second circuit section 70 that runs from the outlet point 38 of the filter element 9 to a collecting bag 15. At the outlet 38 from filter element 9 it flows in a first intermediate pipe 40 fixed to the outlet point 38 of the filter element 9. This first intermediate pipe 40 is connected to a second pressure sensor 10 the measurement from which, in conjunction with the measurement effected by the first pressure sensor 7, indicates the operational status of the filter element 9.

Downstream of this point of connection with the second pressure sensor 10, the first intermediate pipe 40 has a branch connection from which departs a branch pipe 41 fitted with an isolating valve; this branch pipe has at the end a male connector adapted to be connected to an appropriate female connector that is carried by a sampling or a draining bag or even a drain pipe, as shown here. The operator uses these bags if they need to take a sample of the liquid for analysis or to drain the liquid contained in the circuit.

The first intermediate pipe 40 ends in a male connector 42 to which is connected a female connector fixed to one end of a second intermediate pipe 43. This second pipe is connected at its other end to the inlet point 44 of a final filter element 11. The liquid to be treated passes through the final filter 11 to facilitate its subsequent storage.

From the outlet of this final filter element 11, the biological liquid enters a second flexible pipe 12 that is connected to the outlet point 45 of the final filter 11. This second pipe 12 also carries an isolating valve for enabling or preventing circulation of the liquid. Its other end is connected directly to the collecting bag 15 for collecting the treated liquid. Near the bag 15, the pipe 12 includes a Millipore NovaSeal™ element adapted to be crimped and cut in one operation although other sealing mechanisms can be used if desired. Branch connections can also be provided on this second flexible pipe 12 for connecting sampling or draining bags or tanks to it, as required.

The installation that uses the circuit described above is described next with reference to FIGS. 1 and 2. The first cart 1 is mounted on wheels to facilitate moving it in the production area. It is of globally parallelepiped shape, open on one side and at the bottom. Its interior is empty to enable nesting of the second cart 2. On the upper portion of the first cart 1 is a support element, represented in the form of a platform 4, adapted to receive some of the equipment of the circuit, and in particular some of the reusable equipment, and support means for the disposable elements. The reusable elements carried by the platform 4 include the circulation pump 5, represented in the form of a peristaltic pump, the first pressure sensor 7 and a control panel 6 for controlling the pump 5 and various items of equipment mounted on the first cart 1.

In a non-illustrated embodiment, the control panel 6 is mounted on a deformable arm so as to render it possible to adjust the position of the control panel 6.

The platform 4 is positioned at a sufficient height for the second cart 2 to slide under it and be positioned, at least partially, under the circulation pump in the nested configuration.

FIG. 2 shows the pipe 8, an element 8a of which is adapted to cooperate with the pump 5 to circulate the liquid. To simplify the drawing, the circuit sections that follow on from this first pipe and conduct the liquid to be treated through the filter elements are not shown.

FIG. 2 shows a second cart 2, of globally parallelepiped shape, also mounted on wheels, which carries on its upper face 13 re-usable elements such as the second pressure sensor 10 and disposable elements such as the clarification filter element 9 and the final filter element 11. On the cart 2 are seen a number of storage locations here in the form of drawers 14 intended to accommodate the liquid recovery bags or various other containers such as sampling or draining bags, not shown for simplicity.

Figure 6:
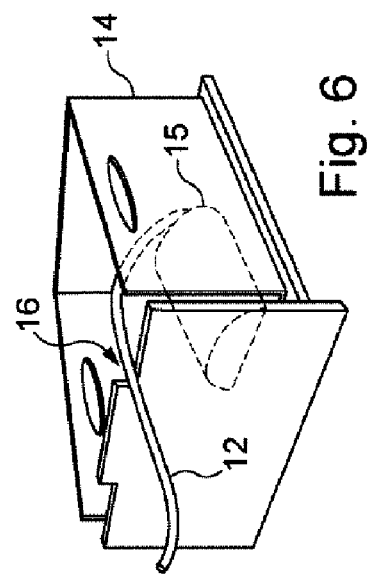
FIG. 6 is a perspective view of a cart drawer.

The liquid to be treated flows in a flexible pipe on the downstream side of the circulation pump 5 and the first pressure sensor 7 in the direction of the clarification filter element 9, and its pressure is then measured by the second pressure sensor 10, which checks that the clarification filter element 9 is working properly. It then enters the final filter element 11, with pores of small diameter, which terminates the operation. The liquid is then sent into the collecting bag 15 positioned inside a drawer 14 of the second cart 2 via a flexible pipe 12 mounted on the outlet orifice of the final filter element 11. The second pipe 12 can pass through the walls of the drawer 14 because a notch 16 is produced in the front of the drawer 14, as can be seen in FIG. 6.

Figure 4:
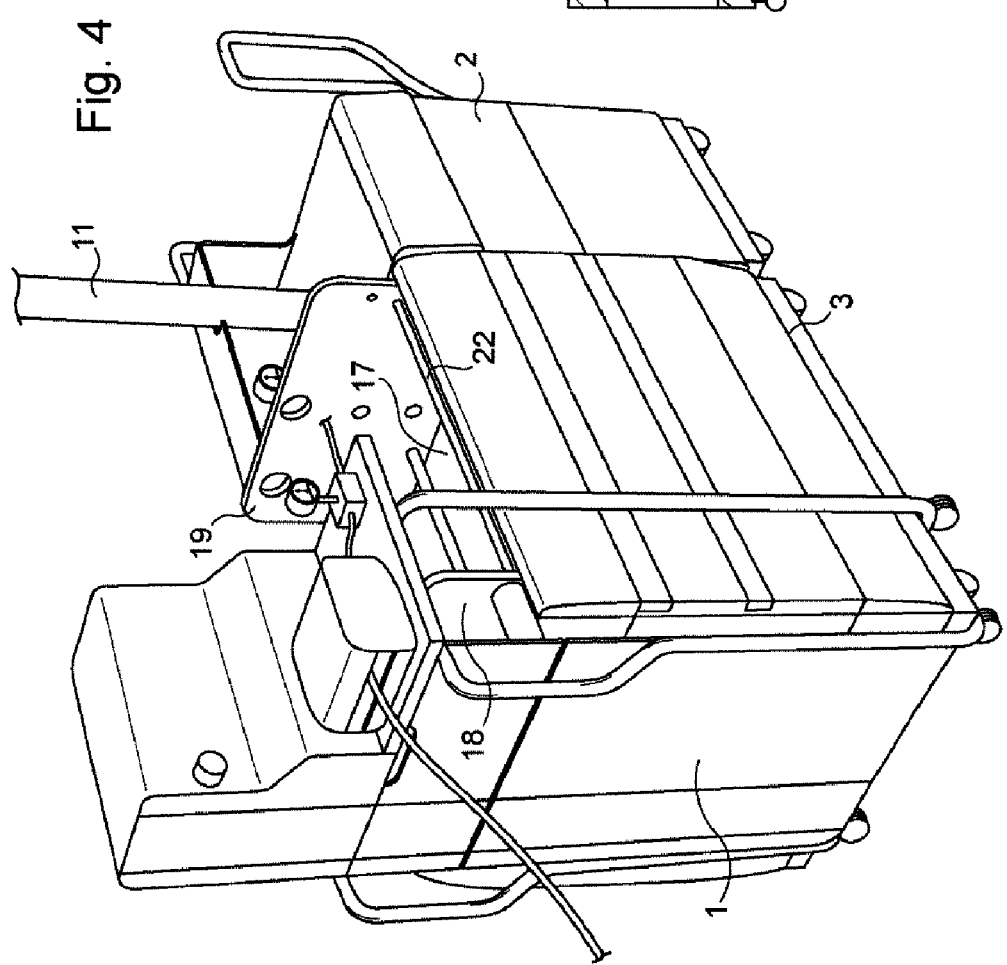
FIG. 4 is a perspective view of this variant, in the nested configuration.

FIGS. 3 to 5 show two variants of the installation, a short version and a long version, in which a third cart 3 is inserted between the first and second carts 1 and 2. In these three figures the device is represented in the nested configuration, i.e. with part of the third cart nested inside the first cart 1.

The third cart 3 is also mounted on wheels and its function is to provide an extension of the cart 2 for treating large volumes of liquid. It has an upper face 17 situated under a support 22 for a large filter element. In these variants the clarification filter element 9 is moved from the second cart 2 onto the third cart 3. The only filter element carried by the second cart is then the final filter element 11.

Figure 7A:
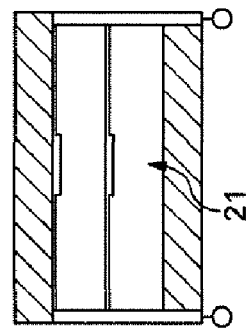
FIGS. 7A and 7B are diagrams showing alternative layouts of the third cart.
Figure 7B:
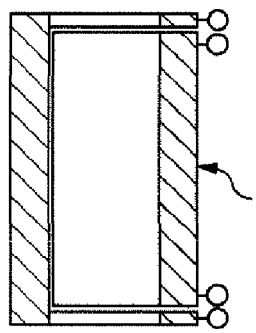

The third cart 3 has on its front face a plurality of storage locations similar to the drawers 14 or alternatively in the form of drawers 21 arranged differently or a tank 23, as shown in FIGS. 7A and 7B. The tank 23 is used in preference to the drawers 14 or 21 when it is necessary to collect a large quantity of liquid and the corresponding weight of the bag is large. To this end the tank 23 is fitted with wheels to facilitate handling in the production area.

The short version of the third cart 3 as shown in FIG. 4 has a simple parallelepiped shape whereas the long version shown in FIG. 5 also has two lateral extensions that project from the parallelepiped and provide a longer upper face 17. This long version can receive filter elements 9 having an even larger filter area. In these two figures the device is shown in the nested configuration, i.e. either the parallelepiped represented in FIG. 4 or one of the extensions represented in FIG. 5 is nested in the first cart 1.

In the short version as in the long version, the third cart 3 has above its upper face 17 two support elements 18 and 19 in the form of plates, between which the clarification filter element 9 is positioned. This filter element, not shown in FIGS. 4 and 5, consists of a stack of known individual filter elements, such as those sold under the trade name Millistak+® POD by Millipore. They are positioned on a filter element support 22 shown in FIGS. 4 and 5 in the form of horizontal bars on which they are laid side by side. They are moreover clamped between a first support element 18 fixed relative to the upper face 17 and a second support element 19 that is adapted to be moved toward the first support element 18 to clamp the individual filter elements together and to provide a seal between them. The individual filter elements are in fluid communication with each other via the corresponding plates 18 and 19 with the flexible pipe for supplying the liquid to be treated and the flexible pipe for evacuating the treated liquid.

The upper face 17 of the third cart is mounted on the upper portion of the cart so that it can slide so that it can be pulled out by the operator like a drawer, for example to clean it. It further has a low point on the same side as the lateral extension that is situated alongside the second cart 2. As shown in FIG. 8, an evacuation plughole 20 is positioned at this low point of the upper face 17. It evacuates liquids that have accumulated on the upper face 17, for example when disassembling the clarification filter element 9, or water used for washing or rinsing this upper face after use. In a variant that is not shown the upper face of the second cart 2 is also mounted on the upper portion of the cart so that it can slide and also has a low point provided with a plughole.

Figure 9:
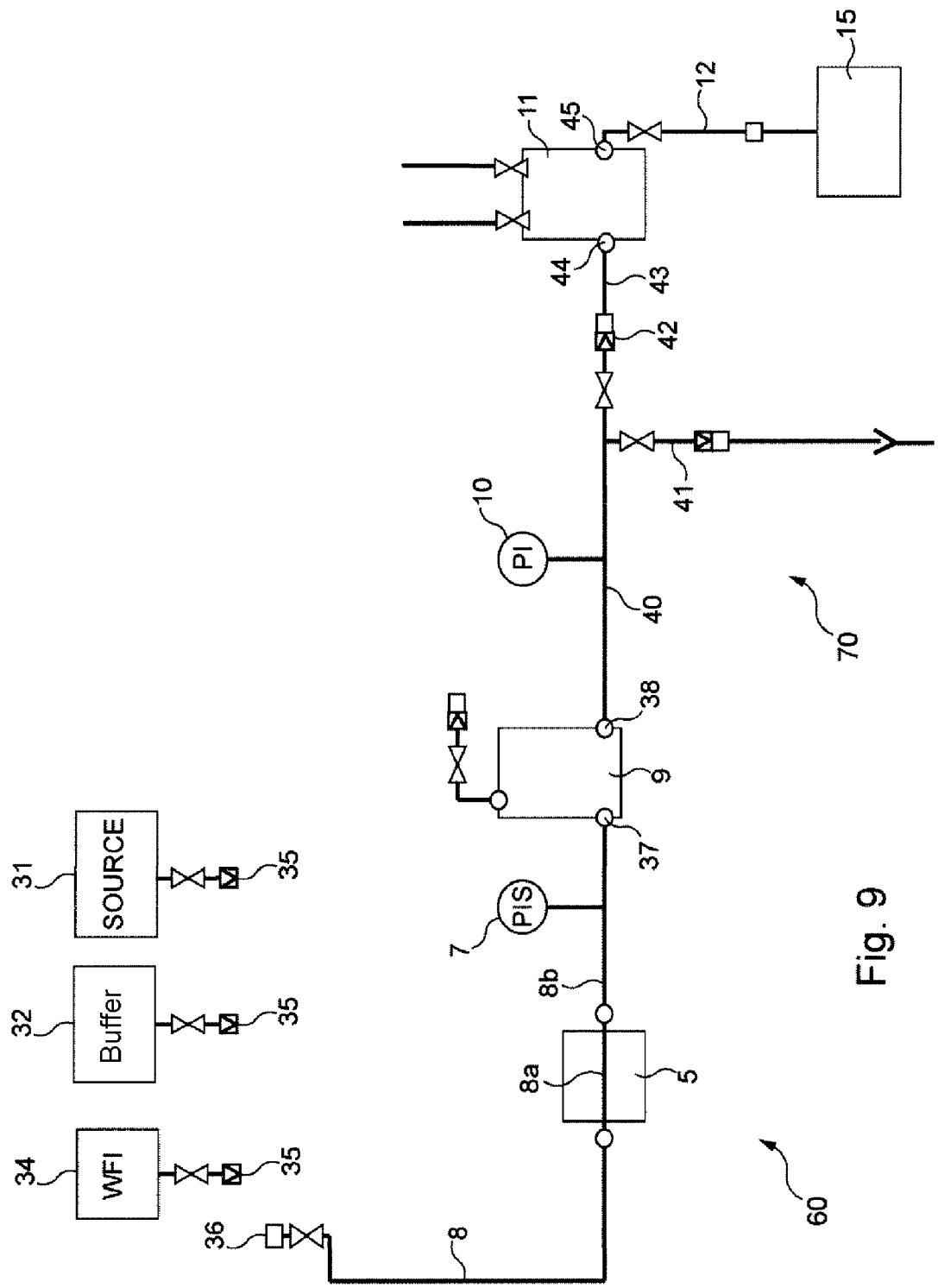
FIG. 9 is a diagram of the liquid circuit of the installation shown in FIGS. 1 and 2 and its variant shown in FIGS. 3 to 5, suitable for a clarification treatment.
Figure 10:
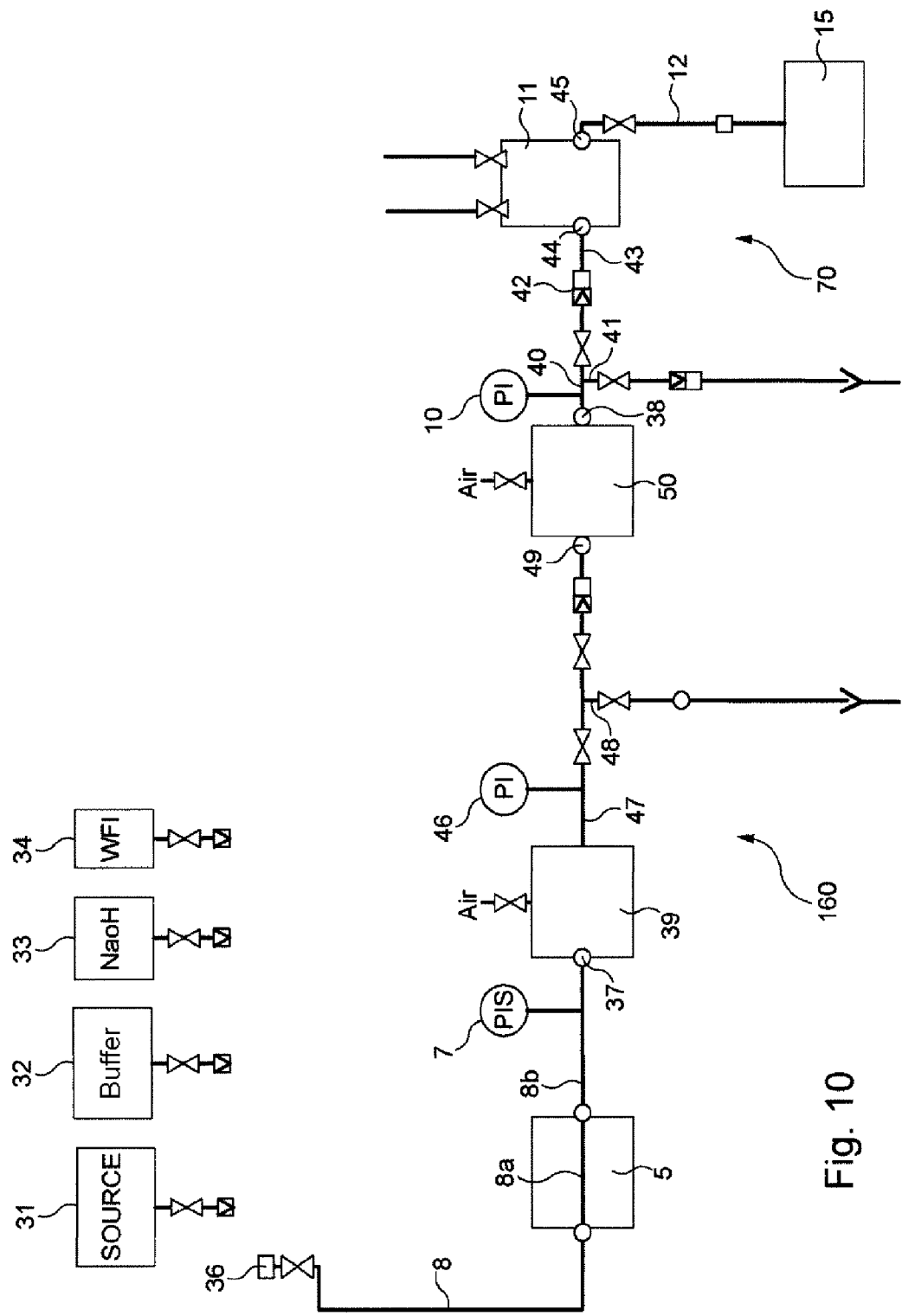
FIG. 10 is a diagrammatic view of an alternative liquid circuit, suitable for a virus retention treatment.

In another embodiment of the invention, represented in FIG. 10, the circuit that is used is adapted for virus retention treatment. This circuit is identical to that of FIG. 9, except that there is shown a supplementary source bag 33 containing NaOH in solution, with a first circuit section 160 extending from the source bag 31 to the inlet point 49 of the filter element 50. Here the liquid to be treated undergoes two stages of filtration, rather than one. It first enters a pre-filter element 39 via the inlet point 37. From the outlet of this element 39 it flows in an intermediate third pipe 47 that is connected to a third pressure sensor 46 the measurement from which, in conjunction with the measurement effected by the first pressure sensor 7, indicates the operational status of the pre-filter element 39.

Downstream of this point of connection with the third pressure sensor 46, the intermediate third pipe 47 has a branch connection from which departs a second branch pipe 48 fitted with an isolating valve; as before, this branch pipe has at its end a male connector adapted to be connected to a suitable female connector that is carried by a sampling bag or a draining bag or even a drain pipe, as shown here.

The intermediate third pipe 47 is connected at its other end to the inlet point 49 of a virus filter forming the filter element 50 that terminates the virus retention operation as such.

The filter element 50 is for instance a Viresolve® filter available from Millipore.

In a non-illustrated variant, the filter element 9 or 50 is replaced by a different filter element, for instance a membrane adsorber such as a ChromaSorb™ available from Millipore.

To the outlet point 38 of this viral filter there is attached a second circuit section 70 identical to that shown in FIG. 9 for the end segment of the clarification treatment.

The final filter 11 in circuit sections 70 is for instance an Opticap® filter capsule available from the company Millipore.

In non-illustrated variants the connectors are of different genders or are genderless, as explained above about connectors 35 and 36.

In other non-illustrated variants, the housings for bags or other containers are different from drawers such as 14, 21 or from tanks such as 23, for instance a tank without wheels or a basket.

Numerous variants are possible as a function of circumstances, and in this regard it is pointed out that the invention is not limited to the examples described and shown.

The invention claimed is:

1. Installation for treating a biological liquid, comprising:
   a circulation pump having an inlet and an outlet;
   a filter element;
   a container for collecting treated liquid;
   a first circuit section connecting a source of said biological liquid to an inlet orifice of said filter element, including a circuit element adapted to cooperate with said circulation pump to circulate said biological liquid in said first circuit section;

a pre-filter element between said outlet of said circulation pump and said inlet orifice of said filter element, said pre-filter element having an inlet and an outlet;

a first pressure sensor in fluid communication with said pre-filter element inlet and a second pressure sensor in fluid communication with said pre-filter outlet;

a second circuit section, connecting an outlet orifice of said filter element to said treated liquid collecting container;

wherein said treated liquid collecting container is a disposable bag, said first circuit section and said second circuit section are disposable and said installation further includes:

a first cart carrying said pump; and a second cart including a housing for said collecting bag, separable from the first cart and adapted to be at least partly nested in said first cart.

2. Installation according to claim 1, wherein when said second cart is nested at least partly in said first cart, said housing for said collecting bag is positioned at least partly under said pump.

3. Installation according to claim 1, wherein said first cart includes a control panel of said pump.

4. Installation according to claim 1, wherein said housing of said second cart is formed by the interior of a drawer.

5. Installation according to claim 4, wherein the front of said drawer includes a notch adapted to have a pipe of said second circuit section pass through it.

6. Installation according to claim 1, wherein the first cart has a length less than that of the second cart.

7. Installation according to claim 1, wherein said first cart has a globally parallelepiped shape open on one side and at the bottom to enable nesting of said second cart.

8. Installation according to claim 1, further comprising a third cart including a support for said filter element and an alternate housing for said collecting bag, said third cart being adapted to be disposed between the first cart and the second cart.

9. Installation according to claim 8, wherein said third cart is adapted to be nested at least partly in said first cart and to be disposed side by side with the second cart.

10. Installation according to claim 8, wherein said alternate housing is a tank on wheels adapted to contain said bag.

11. Installation according to claim 1, wherein at least one of said carts includes a plurality of housings for a disposable bag.

12. Installation according to claim 1, wherein at least one of said carts includes a plate sliding like a drawer and provided with a liquid evacuation plughole.

13. Installation according to claim 1, wherein each of said carts is mounted on wheels.

14. Installation according to claim 1, wherein said second circuit section includes a final filter element between the outlet orifice of said filter element and said collecting bag.

* * * * *